US011672597B2

(12) United States Patent
Tajima et al.

(10) Patent No.: US 11,672,597 B2
(45) Date of Patent: Jun. 13, 2023

(54) MEDICAL DEVICE AND TREATMENT METHOD

(71) Applicant: ALIVAS INC., Tokyo (JP)

(72) Inventors: Tomoyuki Tajima, Tokyo (JP); Shohei Matsuhara, Tokyo (JP); Yoshiki Watabe, Tokyo (JP)

(73) Assignee: ALIVAS INC., Tokyo (JP)

( * ) Notice: Subject to any disclaimer, the term of this patent is extended or adjusted under 35 U.S.C. 154(b) by 28 days.

(21) Appl. No.: 17/395,917

(22) Filed: Aug. 6, 2021

(65) Prior Publication Data
US 2021/0401497 A1 Dec. 30, 2021

Related U.S. Application Data

(63) Continuation of application No. PCT/JP2020/036895, filed on Sep. 29, 2020.

(30) Foreign Application Priority Data

Nov. 20, 2019 (WO) ............... PCT/JP2019/045431

(51) Int. Cl.
A61B 18/18 (2006.01)
A61B 18/00 (2006.01)

(52) U.S. Cl.
CPC ............ A61B 18/1815 (2013.01); A61B 2018/00404 (2013.01); A61B 2018/00994 (2013.01); A61B 2018/1861 (2013.01)

(58) Field of Classification Search
CPC ..... A61B 18/1815; A61B 18/08; A61B 18/12; A61B 18/14; A61B 18/18;
(Continued)

(56) References Cited

U.S. PATENT DOCUMENTS

2012/0010143 A1 1/2012 Suh
2012/0259326 A1* 10/2012 Brannan .......... A61B 17/00234
606/33
(Continued)

FOREIGN PATENT DOCUMENTS

JP 2013544565 A 12/2013
JP 2014-514071 A 6/2014
(Continued)

OTHER PUBLICATIONS

International Search Report for PCT/JP2020/036895 dated Nov. 24, 2020.
(Continued)

Primary Examiner — Thomas A Giuliani
(74) Attorney, Agent, or Firm — Lucas & Mercanti, LLP

(57) ABSTRACT

At a distal portion of a shaft of a guide portion included in a medical device, a first portion is configured to be capable of coming into contact with an inner wall of a living organ. A second portion is disposed on a proximal side of the shaft with respect to the first portion. The second position is configured to be capable of coming into contact with the inner wall of the living organ at a position different from that of the first portion on a transverse cross section of the inner wall of the living organ. A treatment portion is movable in a lumen of the shaft in a state where at least a part of the first portion and at least a part of the second portion come into contact with the inner wall of the living organ.

18 Claims, 14 Drawing Sheets

(58) Field of Classification Search
CPC .. A61B 2018/1846; A61B 2018/00404; A61B 2018/1861; A61B 2018/0022; A61B 2018/00214; A61B 2018/00232; A61B 2018/00273; A61B 2018/00279; A61B 2018/00285; A61B 2018/1435; A61B 2018/1465; A61B 2018/1475; A61B 2018/1487; A61B 2018/1492; A61N 2007/003; A61N 2007/0021; A61N 2007/025; A61N 2007/0047; A61N 7/02
USPC ............ 606/33, 41, 46, 47; 607/98, 99, 101, 607/113, 115, 116, 154, 156
See application file for complete search history.

(56) References Cited

U.S. PATENT DOCUMENTS

| | | |
|---|---|---|
| 2014/0031812 A1 | 1/2014 | Brannan et al. |
| 2014/0066915 A1* | 3/2014 | Zhou ..................... A61B 18/18 606/41 |
| 2014/0276780 A1* | 9/2014 | Fuimaono ......... A61M 25/0158 606/41 |
| 2015/0119867 A1 | 4/2015 | Barman et al. |
| 2015/0126997 A1 | 5/2015 | Beetel et al. |
| 2015/0290427 A1 | 10/2015 | Warnking |
| 2019/0000542 A1 | 1/2019 | Davison et al. |
| 2019/0000543 A1 | 1/2019 | Davison et al. |

FOREIGN PATENT DOCUMENTS

| | | |
|---|---|---|
| JP | 2017123904 A | 7/2017 |
| JP | 2017196461 A | 11/2017 |
| JP | 2019010509 A | 1/2019 |
| WO | 2013134541 A2 | 9/2013 |

OTHER PUBLICATIONS

International Search Report for PCT/JP2019/045431 dated Feb. 4, 2020 and English translation.
Written Opinion of the International Searching Authority for PCT/JP2020/036895 dated Nov. 24, 2020 and English translation.
JPO, Office Action for the corresponding Japanese patent application No. 2021-124376, dated Jul. 19, 2022, with English translation.

* cited by examiner

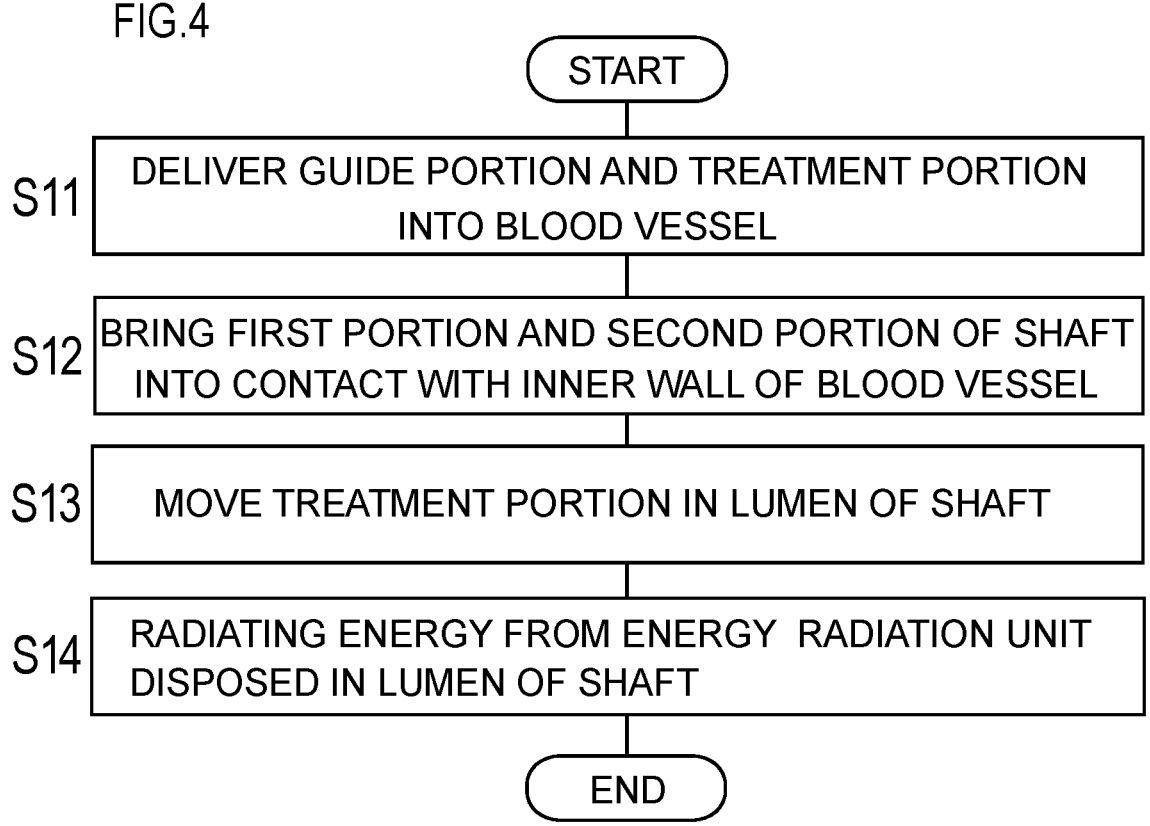
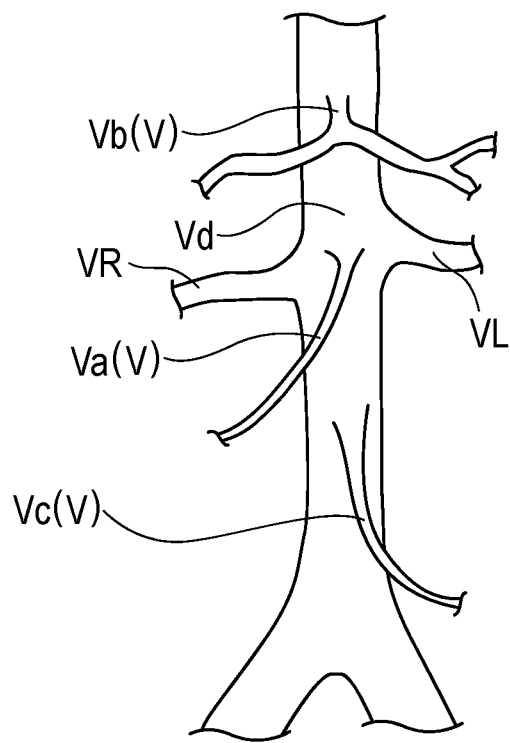

MEDICAL DEVICE AND TREATMENT METHOD

CROSS REFERENCE TO RELATED APPLICATION

This application is a continuation of International Application PCT/JP2020/036895 filed on Sep. 29, 2020 which, in turn, claimed the priority of International Patent Application No. PCT/JP2019/045431 filed on Nov. 20, 2019, both applications are incorporated herein by reference.

TECHNICAL FIELD

The present invention relates to a medical device and a treatment method.

BACKGROUND ART

There is known a medical device used for radiating energy to treat or improve various diseases in a living organ of a human body. As an example of a treatment method using such a medical device, a procedure of ablating a nerve existing outside a blood vessel is performed.

In the medical device used for the above-described procedure, for example, a radio frequency (RF) current may be selected as a type of energy. However, the RF heats an inner wall of the blood vessel directly by Joule's heat, and indirectly increases a temperature of the nerve located outside the blood vessel due to a heat propagation thereof by radiating energy in a state where an energy radiation unit is brought into direct contact with the inner wall of the blood vessel to which the energy is to be applied. Therefore, when the RF is adopted, thermal damage of the directly heated blood vessel is inevitable, and thus, it is necessary to keep the energy low in order to avoid complications such as a perforation of the blood vessel and a stenosis of the blood vessel. Therefore, in the procedure using the RF, an ablation depth has to be shallow, and there is a possibility that denervation cannot be reliably performed. As a measure against the above-described problem, an operator applies energy to a plurality of sites of the blood vessel in a circumferential direction and an extending direction, thereby performing the denervation while avoiding application of the energy locally concentrated on a specific site of the inner wall of the blood vessel.

As a medical device for easily implementing the above-described procedure, an RF catheter or the like including a shaft having a spiral shape and a multipolar electrode arranged on a surface of the shaft has been proposed (see Patent Literature 1).

As another method different from the measure using the RF catheter configured as described above, it is also possible to adopt an energy radiation unit capable of radiating energy such as a microwave or an ultrasonic wave with respect to the inner wall of the blood vessel in a non-contact state and denervating a nerve located outside the blood vessel by using the energy. When such an energy radiation unit is adopted, it is not necessary to bring the energy radiation unit into direct contact with the inner wall of the blood vessel, and thus it is possible to ablate the nerve existing in a deeper portion while protecting the inner wall of the blood vessel from excessive heat damage.

However, since the energy radiation unit (for example, an antenna or an element) that radiates energy as described above is generally larger than an RF electrode, it is difficult to mount a plurality of the energy radiation units on a catheter device or the like having a small diameter. When one energy radiation unit is mounted on the catheter device, in order to denervate a nerve located outside the blood vessel over a predetermined range or more, it is necessary to repeat a procedure in which the energy radiation unit is brought close in a predetermined direction of a transverse cross section of the blood vessel to radiate energy, and then a position of the energy radiation unit is slightly shifted to radiate the energy until reaching a target ablation range. However, in order to perform such a procedure under X-ray fluoroscopy, an advanced catheter operation technique is required, and a treatment success rate varies depending on the operator.

In order to solve the above-described problem, a method has been attempted in which a catheter device equipped with one energy radiation unit is used, and energy is radiated from the energy radiation unit disposed at a center of a transverse cross section of the blood vessel in an entire circumferential direction with a high output (see Patent Literature 2).

CITATION LIST

Patent Literatures

Patent Literature 1: WO 2013-134541 A
Patent Literature 2: JP 2017-196461 A

SUMMARY

Technical Problem

However, when a catheter device of Patent Literature 2 is adopted, a distance between an energy radiation unit and an inner wall of a blood vessel is large at the time of performing a treatment, and thus it is necessary to radiate energy with a high output. In addition, when the energy is radiated from the energy radiation unit with the high output, the energy radiation unit and a transmission path generate heat and a temperature thereof become high. Therefore, an operator needs to actively cool the energy radiation unit during a procedure by perfusion or the like of cooling water. Furthermore, since a diameter of the target blood vessel is different for each patient and for each ablation site, a distance from the energy radiation unit disposed at a center of the blood vessel to the inner wall of the blood vessel is different every time. Therefore, the operator needs to change an output or the like in accordance with a blood vessel diameter. Accordingly, in the catheter device of Patent Literature 2, the device structure becomes complicated, and a workload of the operator, which is required for the procedure, also increases.

The present invention has been made based on the above-described problems, energy can be locally radiated to a treatment target site by bringing the energy radiation unit, which can radiate the energy in a non-contact state with respect to a living organ, close to the treatment target site. As a result, it is possible to perform denervation more reliably by a simpler operation and suppressing an excessive increase in energy radiated from the energy radiation unit.

Solution to Problem

According to an aspect of the present disclosure, there is provided a medical device including: a guide portion that includes a shaft in which a lumen is formed and is insertable into a living organ; and a treatment portion that includes an energy radiation unit capable of radiating energy capable of reaching a surrounding nerve existing outside the living organ, the treatment portion being disposed in the lumen of the shaft, in which a first portion and a second portion are formed at a distal portion of the shaft, the first portion is configured to be capable of coming into contact with an inner wall of the living organ, and the second portion is disposed on a proximal side of the shaft with respect to the first portion and configured to be capable of coming into contact with the inner wall of the living organ at a position different from that of the first portion on a transverse cross section of the inner wall of the living organ, and the treatment portion is movable in the lumen of the shaft in a state where at least a part of the first portion and at least a part of the second portion come into contact with the inner wall of the living organ.

According to another aspect of the present disclosure, there is a treatment method including: inserting a guide portion into a living organ, the guide portion including a shaft in which a lumen is formed; bringing a first portion formed at a distal portion of the shaft into contact with an inner wall of the living organ and bringing a second portion formed on a proximal side of the shaft with respect to the first portion into contact with a position different from that of the first portion on a transverse cross section of the inner wall of the living organ; moving a treatment portion including an energy radiation unit by a predetermined distance along the lumen of the shaft in a state where at least a part of the first portion and at least a part of the second portion are brought into contact with the inner wall of the living organ; and applying energy to a surrounding nerve existing outside the living organ by causing the energy to be radiated from the energy radiation unit in a state where the energy radiation unit is disposed in the lumen of the shaft.

According to the present disclosure, the shaft can be held with respect to the living organ by bringing the first portion of the shaft of the guide portion and the second portion of the shaft of the guide portion into contact with the inner wall of the living organ. In a state where the shaft is held with respect to the living organ, the operator can locally radiate the energy to a predetermined treatment target site (for example, a surrounding nerve positioned outside the blood vessel) by moving the treatment portion along the lumen of the shaft and disposing the energy radiation unit of the treatment portion at the position close to the inner wall of the living organ. Therefore, by suppressing the energy radiated from the energy radiation unit to a low level, the operator can more reliably perform denervation while preventing an occurrence of a burn or the like.

BRIEF DESCRIPTION OF DRAWINGS

FIG. 4 is a flowchart schematically illustrating a procedure of a treatment method according to an embodiment.

FIG. 5 is a view schematically illustrating a blood vessel to which a treatment method is applied.

DESCRIPTION OF EMBODIMENTS

Hereinafter, embodiments of the present invention will be described with reference to the accompanying drawings. Note that, the following description does not limit the technical scope or meaning of terms described in the claims. In addition, dimensional ratios of the drawings are exaggerated for convenience of the description, and may be different from actual ratios. In addition, a range "X to Y" indicated in the present specification means "X or more and Y or less".

Figure 1:
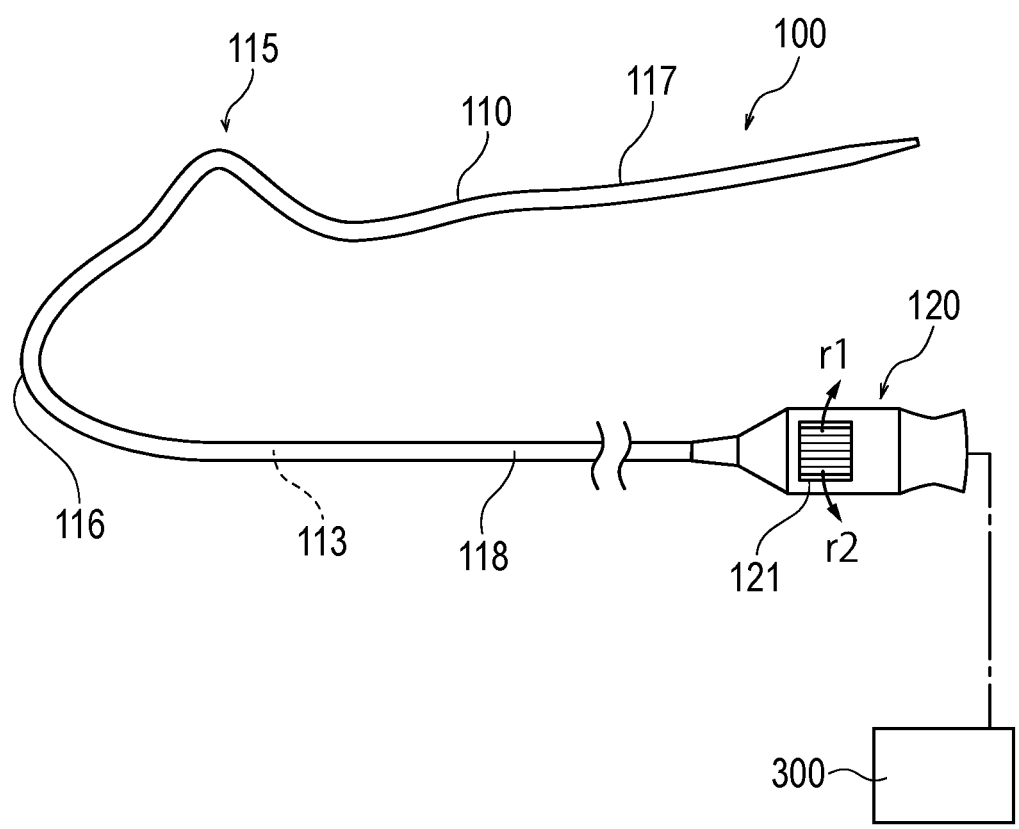
FIG. 1 is a view schematically illustrating an overall configuration of a medical device according to an embodiment.
Figure 2:
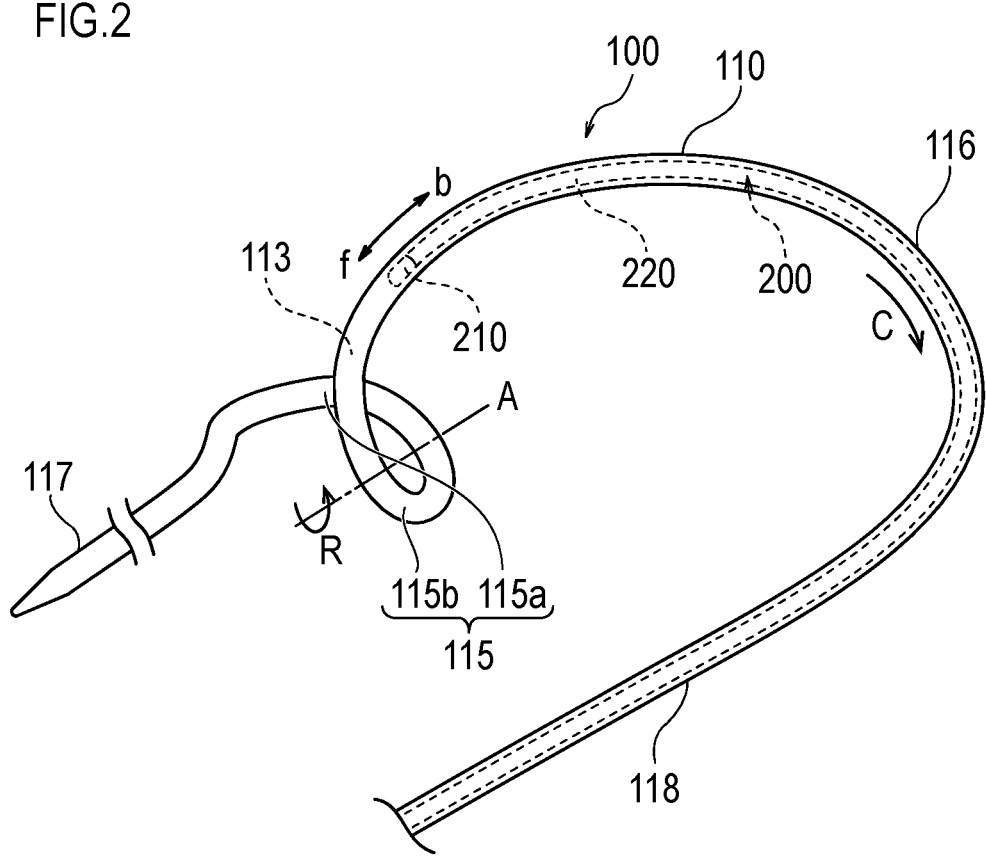
FIG. 2 is an enlarged perspective view illustrating a distal portion of a shaft.
Figure 3:
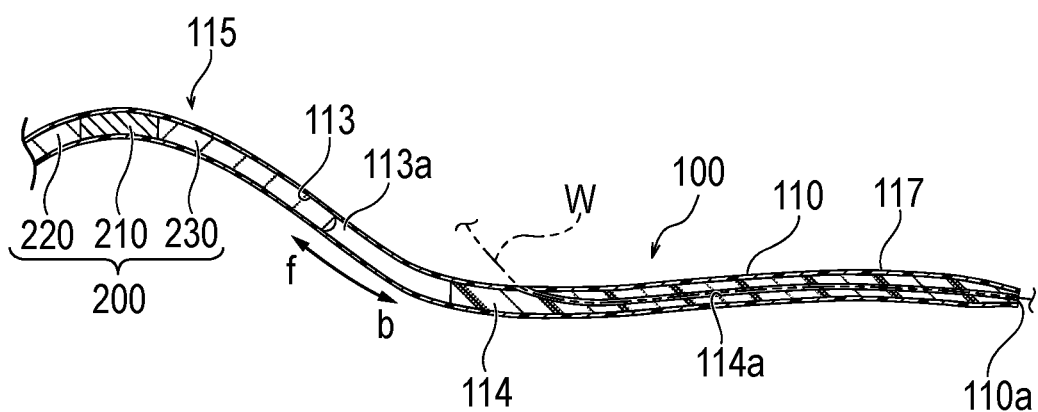
FIG. 3 is a cross-sectional view of a distal portion of a shaft.
Figure 8:
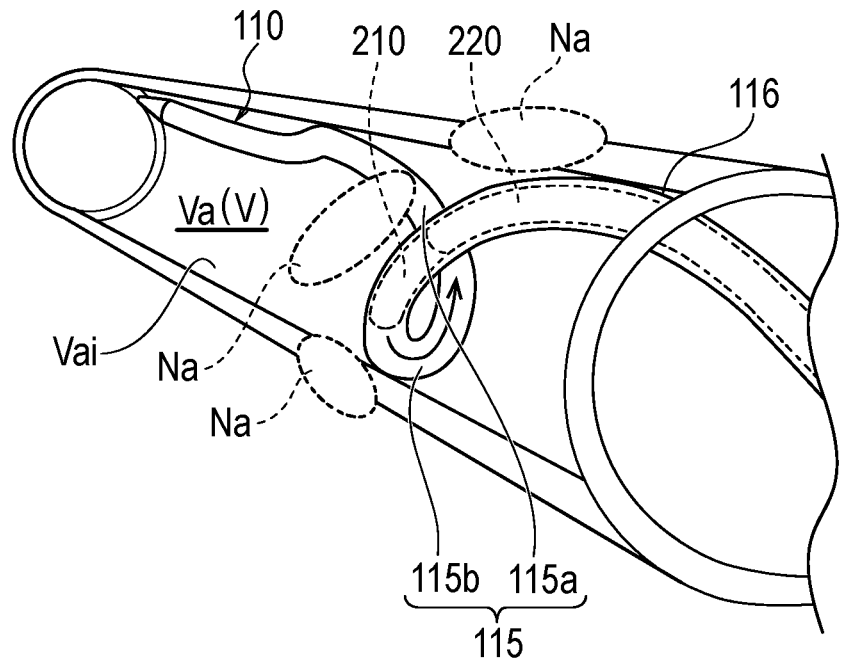
FIG. 8 is a perspective view schematically illustrating a state when a treatment method using a medical device according to an embodiment is performed.
Figure 9:
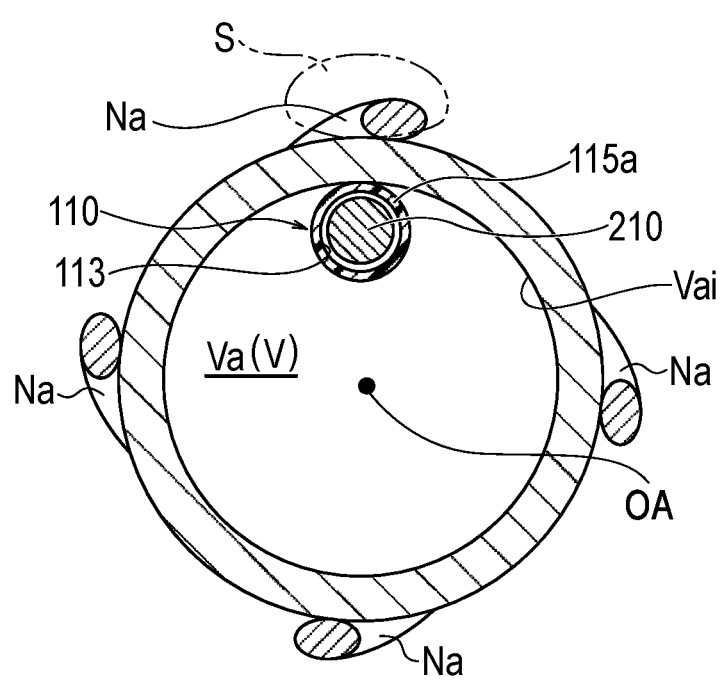
FIG. 9 is a cross-sectional view (transverse cross-sectional view) of a blood vessel taken along an arrow 9A-9A illustrated in FIG. 7.

FIGS. 1 to 3 are views for illustrating each portion of a medical device 10 according to the embodiment. FIG. 4 is a flowchart illustrating an example of a procedure of a treatment method using the medical device 10. FIG. 5 is a view for illustrating a blood vessel V which is a target of a treatment method using the medical device 10. FIGS. 6 to 9 are views for illustrating a usage example of the medical device 10. Note that, FIG. 8 is a perspective view schematically illustrating a state when a guide portion 100 and a treatment portion 200 are disposed in the blood vessel V, and FIG. 9 is a transverse cross-sectional view of the blood vessel V taken along a direction indicated by an arrow 9A-9A in FIG. 7.

<Treatment Target Site>

A treatment target site S will be described with reference to FIGS. 5 to 7. In FIG. 5, a reference sign VR indicates a right renal artery, and a reference sign VL indicates a left renal artery. In addition, in FIG. 5, a reference sign Va indicates a superior mesenteric artery, a reference sign Vb indicates a celiac artery, a reference sign Vc indicates an inferior mesenteric artery, and a reference sign Vd indicates an aorta.

In the treatment method according to the embodiment, an operator such as a medical doctor (hereinafter, referred to as "operator") enhances a peristaltic movement of a gastrointestinal tract by performing a treatment for reducing an activity of an autonomic nerve in the blood vessel V having a surrounding nerve (extravascular nerve) Na that innervates the gastrointestinal tract of a patient. By performing such a treatment, the operator can promote alleviation of at least one symptom of abdominal distension, abdominal pain, perineum discomfort, and frequent defecation desire, which are caused by constipation and/or an abnormality of the peristaltic movement of the gastrointestinal tract of the patient (at least one of a group of symptoms caused by the alleviation of the constipation of the patient and/or the abnormality of the peristaltic movement of the gastrointestinal tract).

The blood vessel V to which the treatment method is applied is not particularly limited as long as the peristaltic movement of the gastrointestinal tract of the patient (subject) can be enhanced by performing a predetermined treatment according to the embodiment (for example, application of energy by a microwave to be described later). As an example, in the blood vessel V, for example, at least one of a superior mesenteric artery Va, a celiac artery Vb, and an inferior mesenteric artery Vc can be suitably selected. In particular, from a viewpoint of more effectively enhancing the peristaltic movement of the gastrointestinal tract after the treatment, it is preferable to select the superior mesenteric artery Va as the blood vessel V.

The operator, as the treatment according to the embodiment, applies energy to one surrounding nerve Na or a plurality of surrounding nerves Na. Accordingly, the operator enhances the peristaltic movement of the gastrointestinal tract by impairing the surrounding nerve Na and completely or partially blocking an autonomic neural transmission to a digestive tract, which is caused by the surrounding nerve Na. The following mechanism is considered as the reason why the peristaltic movement of the gastrointestinal tract is activated by performing the treatment for reducing the activity of the autonomic nerve as described above in the blood vessel V.

When the surrounding nerve Na is impaired by the energy radiated from the inside of the blood vessel V and the autonomic neural transmission to the digestive tract, which is caused by the surrounding nerve Na, is completely or partially blocked, a sympathetic nervous system is relatively attenuated and the parasympathetic nervous system becomes dominant. In addition, when a neural transmission from a central nervous system is blocked, an enteric nervous system that autonomously controls a gastrointestinal movement becomes dominant, and the peristaltic movement of the gastrointestinal tract is accelerated. Furthermore, when the peristaltic movement of the gastrointestinal tract is accelerated, a colonic transit time is promoted and normalized, and thus alleviation of at least one symptom of abdominal distension, abdominal pain, perineum discomfort, and frequent defecation desire, which are caused by constipation and/or an abnormality of the peristaltic movement of the gastrointestinal tract is promoted.

In particular, in the treatment method according to the embodiment, in functional constipation without an organic abnormality in a colon, it is possible to suitably promote the alleviation of the symptoms of a slow-transit constipation in which an intestinal peristaltic movement of a colon decreases, and thus a transit time of stool is delayed and constipation occurs.

Figure 6:
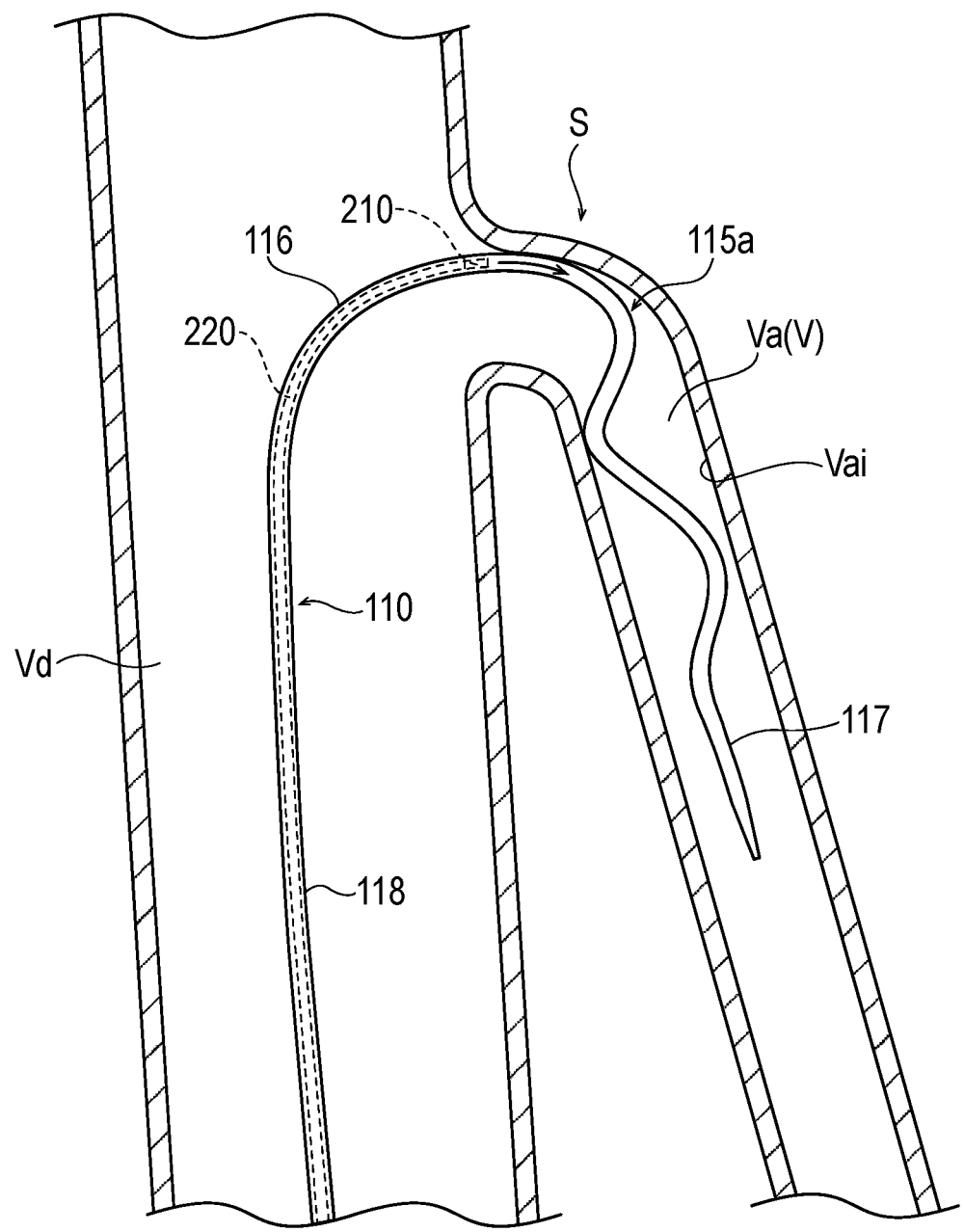
FIG. 6 is a cross-sectional view of a blood vessel schematically illustrating a state when a treatment method using a medical device according to an embodiment is performed.

The treatment target site (region including one or a plurality of surrounding nerves Na) S illustrated in FIG. 6 is not particularly limited as long as the peristaltic movement of the gastrointestinal tract can be enhanced. For example, in the blood vessel V, the treatment may be performed on an arbitrary range (site) in a traveling direction (extending direction) of the blood vessel V, or the treatment may be performed on an arbitrary range (site) in a circumferential direction (circumferential direction of the transverse cross section) of the blood vessel V. In addition, the treatment may be performed on a plurality of arbitrary sites of the same blood vessel V a plurality of times, or may be performed on arbitrary sites of a plurality of different blood vessels V a plurality of times.

In the embodiment, as illustrated in FIGS. 6 to 9, a treatment method in which the superior mesenteric artery Va is used as the target blood vessel V will be described.

The treatment method according to the embodiment includes performing a treatment around an origin of the superior mesenteric artery Va.

It is preferable that the treatment target site S includes, for example, a range of 0 mm to 20 mm along the extending direction of the superior mesenteric artery Va with an opening of the superior mesenteric artery Va as a reference. By applying energy within the above-described range of the superior mesenteric artery Va, it is possible to effectively suppress energy transmission to organs (for example, pancreas or duodenum) located on a peripheral side of the superior mesenteric artery Va.

From a viewpoint of more reliably suppressing the energy transmission to the organs located on the peripheral side of the superior mesenteric artery Va, it is still more preferable that application of the energy from the superior mesenteric artery Va is performed only within the range of 0 mm to 20 mm along the extending direction of the superior mesenteric artery Va.

In addition, as in the treatment method according to the embodiment, when the energy is applied to the treatment target site S from the superior mesenteric artery Va, a range of 0 mm to 100 mm along the extending direction of an aorta Vd with a bifurcation of the superior mesenteric artery Va as a reference may be included in the treatment target site S.

It is preferable that a reaching depth of the energy from the superior mesenteric artery Va side is included in a range of 1 mm to 6 mm from an intima of the superior mesenteric artery Va. The surrounding nerve Na existing outside the superior mesenteric artery Va exists at a relatively deep position around the origin of the superior mesenteric artery Va. More specifically, the surrounding nerves Na exist as a bundle within an adipose tissue outside the superior mesenteric artery Va in a state of being supported by a connective tissue. Therefore, when the energy is applied around the origin of the superior mesenteric artery Va, by causing the energy to reach a position of 1 mm to 6 mm from the intima of the superior mesenteric artery Va, the surrounding nerves Na of the superior mesenteric artery Va can be efficiently denervated.

<Medical Device>

As illustrated in FIGS. 1, 2, and 3, the medical device 10 according to the embodiment includes a guide portion 100, and a treatment portion 200.

As illustrated in FIG. 1, the guide portion 100 includes a shaft 110 and a hub 120 disposed at a proximal end portion of the shaft 110. As illustrated in FIG. 3, the treatment portion 200 includes an energy radiation unit 210, a main body portion 220, and an auxiliary member 230.

In the embodiment, as illustrated in FIG. 1, the medical device 10 can be configured as a catheter device in which the guide portion 100 and the treatment portion 200 are integrally assembled.

<Guide Portion>

The guide portion 100 includes the shaft 110 in which a lumen 113 (see FIG. 9) is formed. The shaft 110 is configured to be insertable into the blood vessel V.

FIG. 2 illustrates the shaft 110 in a natural state in which an external force is not applied. In the natural state, at least a part of a distal portion of the shaft 110 extends along an axial direction of the shaft 110. Note that, the distal portion of the shaft 110 is an end portion of the shaft 110 positioned on a side of an insertion direction into the living body.

As illustrated in FIGS. 2, 8, and 9, a first portion 115a and a second portion 115b are formed at the distal portion of the shaft 110.

As illustrated in FIGS. 8 and 9, the first portion 115a is configured to be capable of coming into contact with an inner wall Vai of the blood vessel V.

The second portion 115b is disposed on a proximal side of the shaft 110 with respect to the first portion 115a.

As illustrated in FIGS. 8 and 9, the second portion 115b is configured to be capable of coming into contact with the inner wall Vai of the blood vessel V at a position different from that of the first portion 115a in the transverse cross section of the inner wall Vai of the blood vessel V.

In the embodiment, a spiral portion 115, in which a part of the shaft 110 extends spirally, is formed at the distal portion of the shaft 110.

Each of the first portion 115a and the second portion 115b is formed as a part of the spiral portion 115. Note that, in the shaft 110 in which the spiral portion 115 is formed, the first portion 115a and the second portion 115b can be defined at arbitrary portions in an extending direction and a circumferential direction of the spiral portion 115.

The spiral portion 115 can have, for example, a counterclockwise direction shape indicated by an arrow R with respect to a predetermined reference axis A. The reference axis A can be defined by, for example, a straight line extending parallel to a proximal side portion 118 of the shaft 110, which extends linearly.

A specific shape of the spiral portion 115 (for example, a pitch of the spiral, the number of turns, an outer diameter of the spiral, a winding direction of the spiral, and the like) is not particularly limited as long as the first portion 115a and the second portion 115b can be brought into contact with the inner wall Vai of the blood vessel V when the shaft 110 is disposed in the blood vessel V.

As illustrated in FIG. 8, the shaft 110 is configured such that a portion from the first portion 115a to the second portion 115b is continuously brought into contact with the inner wall Vai of the blood vessel V in a state of being inserted into the blood vessel V.

As described above, the first portion 115a and the second portion 115b are formed as a part of the spiral portion 115. When inserted into the blood vessel V, the spiral portion 115 extends spirally in the blood vessel V and comes into contact with the inner wall Vai of the blood vessel V in a continuous state in a predetermined range.

The first portion 115a and the second portion 115b included in the spiral portion 115 come into contact with the inner wall Vai of the blood vessel V at different positions respectively in the extending direction of the blood vessel V. In addition, the first portion 115a and the second portion 115b come into contact with the inner wall Vai of the blood vessel V at different positions respectively in the circumferential direction of the blood vessel V. In this manner, the shaft 110 can be disposed at the position at which the first portion 115a and the second portion 115b are close to the inner wall Vai of the blood vessel V.

The operator can selectively dispose the energy radiation unit 210 at an arbitrary position of the spiral portion 115 by moving the energy radiation unit 210 along the spiral portion 115 in a state where the first portion 115a and the second portion 115b are disposed in the blood vessel V as described above.

Then, the operator can locally apply the energy to the surrounding nerve Na from a position close to the inner wall Vai of the blood vessel V by causing the energy to be radiated from the energy radiation unit 210 in a state where the energy radiation unit 210 is disposed at an arbitrary position of the spiral portion 115.

Note that, when the spiral portion 115 is formed in the shaft 110, a part of the shaft 110 has a three-dimensional shape. Therefore, the shaft 110 can secure a larger contact area of the shaft 110 with respect to the inner wall Vai of the blood vessel V. As a result, the shaft 110 is more stably held with respect to the blood vessel V.

In addition, when the spiral portion 115 is formed in the shaft 110, the energy radiation unit 210 can be disposed at an arbitrary position in the extending direction of the blood vessel V and the circumferential direction of the blood vessel V in a range in which the spiral portion 115 is formed (portion from the first portion 115a to the second portion 115b). Therefore, the energy can be easily and efficiently applied to the surrounding nerve Na from a position close to the inner wall Vai of the blood vessel V.

The shaft 110 is formed in advance so as to have a shape in which the spiral portion 115 illustrated in FIG. 2 is formed.

Note that, for example, the shaft 110 may be configured so as to be formed substantially linearly as a whole when introduced into a living body, and to be deformed into the shape illustrated in FIG. 2 when delivered to the blood vessel V. When the shaft 110 is configured in this manner, for example, the shaft 110 can be configured to be reversibly deformed into a linear shape and a shape in which the spiral portion 115 is formed by inserting a member such as a guide wire W having higher rigidity than that of the shaft 110 over the entire length of the shaft 110, and then applying and releasing a physical force. In addition, when the shaft 110 is configured in this manner, the shaft 110 can be provided with a guide wire lumen formed over the entire length of the shaft 110 in a lumen through which the treatment portion 200 is inserted.

In addition, the shaft 110 can be made of, for example, a material or the like having temperature responsiveness that deforms a part of the shaft 110 according to a temperature change or the like, and can be configured such that the spiral portion 115 is formed by adjusting the temperature.

As illustrated in FIGS. 2 and 6, the shaft 110 includes a curved portion 116 positioned on the proximal side with respect to the second portion 115b.

The curved portion 116 can be configured by deflecting a portion positioned on the distal side of the shaft 110 with respect to the curved portion 116 with respect to a portion positioned on the proximal side of the shaft 110 with respect to the curved portion 116.

In the embodiment, the curved portion 116 has a shape curved such that a part of the shaft 110 is folded toward the proximal side portion 118. A folding direction of the curved portion 116 is indicated by an arrow C in FIG. 2. Note that, in the shaft 110, the position where the curved portion 116 is provided or the specific shape (curved direction, curvature, length, and the like) of the curved portion 116 are not particularly limited.

Figure 7:
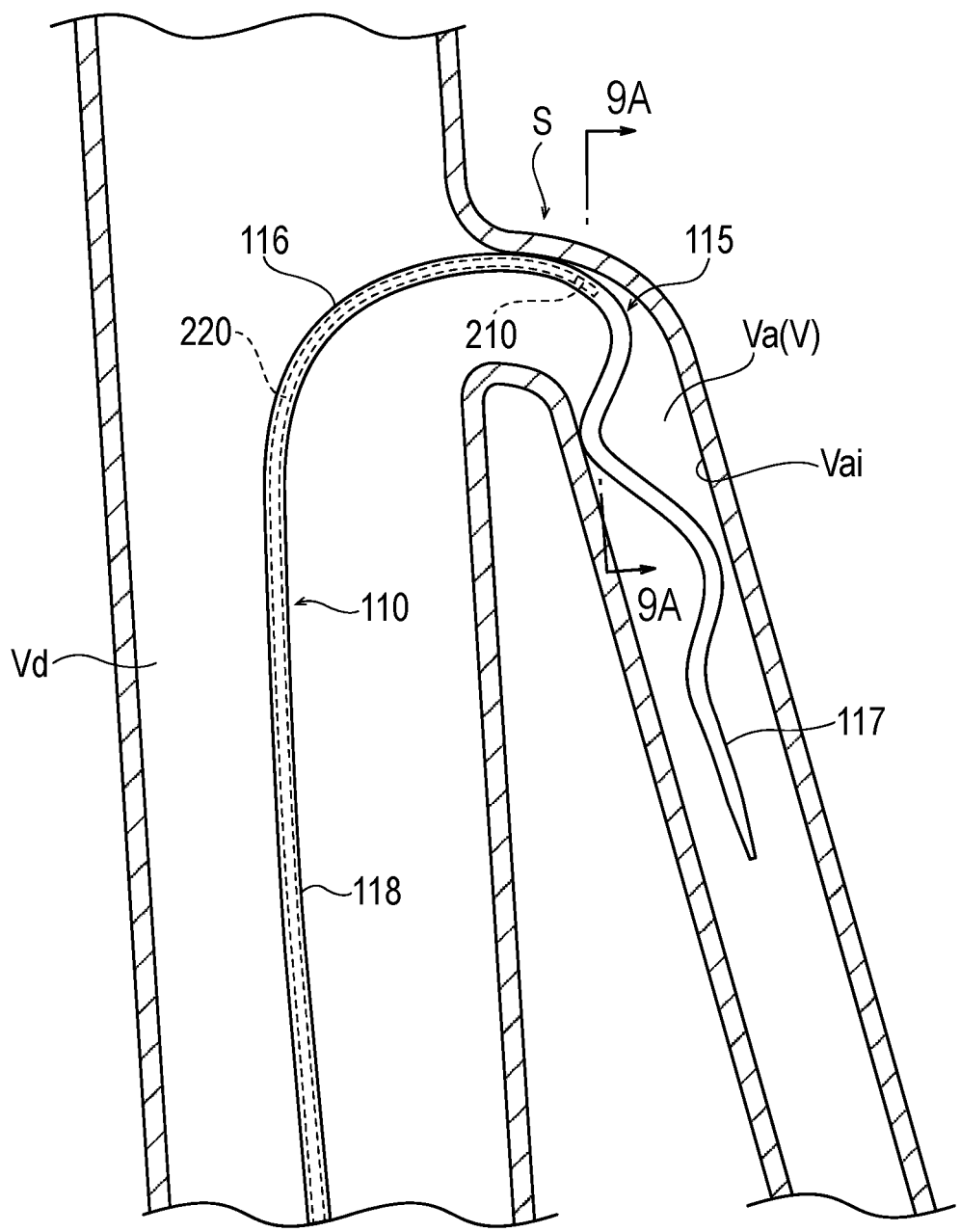
FIG. 7 is a cross-sectional view of a blood vessel schematically illustrating a state when a treatment method using a medical device according to an embodiment is performed.

As illustrated in FIGS. 6 and 7, the superior mesenteric artery Va is branched from the aorta Vd and then is steeply bent in a direction of a lower limb, and runs substantially in parallel with the aorta Vd. Therefore, when the treatment using the medical device 10 is performed by transfemoral approach, it is not easy to deliver the medical device 10 into the superior mesenteric artery Va.

In the embodiment, by the curved portion 116 formed on the proximal side of the shaft 110 with respect to the second portion 115b, a portion positioned on the distal side of the shaft 110 can be deflected with respect to a portion positioned on the proximal side of the shaft 110 with respect to the curved portion 116. Therefore, even in an approach from the lower limb side via the aorta Vd, it is easy to introduce the portion positioned on the distal side of the shaft 110 into the superior mesenteric artery Va.

When delivering the medical device 10 by transfemoral approach to the superior mesenteric artery Va, for example, the operator can insert the medical device 10 into a femoral artery from a groin of the patient, and move the medical device 10 to the aorta Vd. By adopting this route, an insertion length of the medical device 10 in the living body is short. Therefore, the operator can operate the medical device relatively easily in the living body. In the procedure using the medical device 10, when accessing the superior mesenteric artery Va from the lower limb side, the curved portion 116 may come into contact with the inner wall Vai of the blood vessel V located around the origin of the superior mesenteric artery Va. As a result, a holding force of the shaft 110 with respect to the inner wall Vai of the blood vessel V can be increased.

As illustrated in FIGS. 1, and 2, the shaft 110 includes a distal side portion 117 disposed on the distal side of the first portion 115a, and a proximal side portion 118 disposed on the proximal side of the curved portion 116.

As illustrated in FIG. 1, the distal side portion 117 extends in a direction away from the proximal side portion 118 in a natural state where an external force is not applied. For example, a distal end tip can be attached to a distal end of the distal side portion 117. The distal end tip can be made of, for example, a resin material having flexibility.

The proximal side portion 118 extends substantially linearly. The hub 120 is attached to a proximal end of the proximal side portion 118.

As illustrated in FIG. 1, the hub 120 includes an operation unit 121 that allows the main body portion 220 (see FIG. 3) of the treatment portion 200 to relatively move slidingly in the shaft 110 by a hand operation.

The operation unit 121 is mechanically connected to the treatment portion 200 inserted into the lumen 113 of the shaft 110. For example, the operation unit 121 can be configured to cause the treatment portion 200 to move slidingly in the lumen 113 of the shaft 110 with a rotating operation in a direction of arrows r1 and r2 illustrated in FIG. 1.

Note that, for example, the operation unit 121 may be configured to cause the treatment portion 200 to move slidingly by advancing and retreating the operation unit 121 in conjunction with the advancing and retreating movement thereof, and include a lock mechanism that fixes a position before and after the movement of the treatment portion 200.

As illustrated in FIG. 3, a filling member 114 can be disposed at a distal portion of the lumen 113 of the shaft 110. A space portion 113a that allows a movement of the treatment portion 200 can be provided on the proximal side of the filling member 114. The filling member 114 partitions a region in which the treatment portion 200 is accommodated in the lumen 113 and a region in which a guide wire lumen 114a is formed in the lumen.

Inside the filling member 114, the guide wire lumen 114a through which the guide wire W can be inserted can be formed. The guide wire lumen 114a communicates between an arbitrary position of the distal side portion 117 positioned on the distal side of the shaft 110 and a distal end opening portion 110a of the shaft 110. That is, the medical device 10 is configured as a monorail-type catheter device in which the guide wire lumen 114a is formed only on the distal side of the shaft 110.

The shaft 110 can be made of a member having flexibility. The material used for the shaft 110 is not particularly limited, but for example, the same material as a resin material used for a known catheter device can be used.

The shaft 110 may be formed of, for example, a single-layer or multi-layer resin tube member, or a blade wire or the like for reinforcing rigidity may be embedded in the shaft 110. In addition, a coating such as a hydrophilic coating may be applied to an outer surface of the shaft 110. An outer diameter, an inner diameter, an axial length, a cross-sectional shape, and the like of the shaft 110 are not particularly limited.

The material of the filling member 114 filled in the shaft 110, the axial length in which the filling member 114 is filled, an axial length or position of the space portion 113a, and the like are not particularly limited.

<Treatment Portion>

As illustrated in FIGS. 3 and 9, the treatment portion 200 includes the energy radiation unit 210 capable of radiating energy that can reach the surrounding nerve Na located outside the blood vessel V in a state of being disposed in the lumen 113 of the shaft 110, and the main body portion 220 in which the energy radiation unit 210 is disposed at the distal portion and which is inserted into the lumen 113 of the shaft 110.

As illustrated in FIGS. 6, 7, and 8, the treatment portion 200 is movable in the lumen 113 of the shaft 110 in a state where at least a part of the first portion 115a of the shaft 110 comes into contact with the inner wall Vai of the blood vessel V.

An arrow f in FIGS. 2 and 3 indicates a direction in which the treatment portion 200 advances along the lumen 113 of the shaft 110. An arrow b indicates a direction in which the treatment portion 200 retreats along the lumen 113 of the shaft 110.

The energy radiation unit 210 can be configured to be capable of radiating, for example, a microwave or an ultrasonic wave.

When the energy radiation unit 210 is configured to be capable of radiating the microwave, the energy radiation unit 210 can be configured by, for example, an antenna element.

In the energy radiation unit 210, when the energy radiation unit 210 is configured by the antenna element, a center frequency of the antenna element can be set to, for example, any of 915 MHz, 2.45 GHz, 5.8 GHz, and 24.125 GHz.

When the energy radiation unit 210 is configured to be capable of radiating the ultrasonic wave, the energy radiation unit 210 can be configured by, for example, an ultrasonic element.

As long as the energy radiation unit 210 can radiate energy from the lumen 113 of the shaft 110 and cause the energy to reach the surrounding nerve Na existing outside the blood vessel V to denervate a nerve, a specific structure, a type of the radiated energy, a maximum output of the energy, and the like are not particularly limited. However, even when the energy is applied in a state of not coming into direct contact with the inner wall Vai of the blood vessel V, it is preferable that the energy radiation unit 210 is configured to be capable of radiating the microwave and the ultrasonic wave such that the surrounding nerve Na existing outside the blood vessel V can be more reliably denervated.

For example, when the energy radiation unit 210 is configured by an antenna element, the main body portion 220 of the treatment portion 200 can be configured by a known coaxial cable through which a current can be supplied to the antenna element. Note that, as long as the main body portion 220 is movable in the lumen 113 in a state of being inserted into the lumen 113 of the shaft 110, the specific configuration is not particularly limited. For example, the main body portion 220 can be configured to have any structure according to a structure of the energy radiation unit 210.

Only one energy radiation unit 210 can be provided in the treatment portion 200. By setting the number of the energy radiation units 210 provided in the treatment portion 200 to only one, a diameter of the main body portion 220 can be reduced. Furthermore, by reducing the diameter of the main body portion 220, it is possible to reduce a diameter of the lumen 113 of the shaft 110 into which the main body portion 220 is inserted. As a result, an outer diameter of the shaft 110 can be reduced.

As illustrated in FIG. 3, the treatment portion 200 includes an auxiliary member 230 disposed on the distal side of the energy radiation unit 210.

When the energy radiation unit 210 moves in the lumen 113 of the shaft 110, the auxiliary member 230 slides in the shaft 110 to assist the movement of the energy radiation unit 210.

The auxiliary member 230 assists the movement of the energy radiation unit 210 on the distal side of the energy radiation unit 210. Therefore, the operator can smoothly move the energy radiation unit 210 along the first portion 115a formed spirally. The auxiliary member 230 can be made of, for example, a resin material. Note that, in the drawings other than FIG. 3, the auxiliary member 230 is not illustrated.

The space portion 113a of the lumen 113, which is formed on the distal side of the auxiliary member 230, defines the movement amount of the treatment portion 200 and an advance limit position of the treatment portion 200.

The treatment portion 200 can advance to a position coming into contact with the proximal end of the filling member 114 disposed on the distal side of the space portion 113a. Therefore, it is possible to prevent the treatment portion 200 from unnecessarily moving to the distal side of the shaft 110. Accordingly, the operator can easily move the energy radiation unit 210 within a range in which the spiral portion 115 is formed.

The radiation of energy by the energy radiation unit 210 can be controlled, for example, by a predetermined controller (control device) 300 illustrated in FIG. 1. The controller 300 can be connected to the energy radiation unit 210 via, for example, an energy transmission mechanism such as a signal wire or an electric wire guided from the hub 120.

As the controller 300, for example, a known control device including a CPU and a storage unit can be used.

The storage unit includes a ROM that stores various programs and data, a RAM that temporarily stores programs and data as a work area, a hard disk that can store various programs and data, and the like.

The storage unit can store a series of programs necessary for an operation control of the treatment portion 200.

Examples of a transmission form of an operation command to the treatment portion 200 can include wired transmission via a telecommunication line, wireless transmission without the telecommunication line, transmission based on an input from an operator or the like via an operation unit incorporated in the controller, and transmission based on an input from external communication means or the like prepared as a device separate from the controller, but the specific form is not particularly limited.

The treatment using the energy radiation unit 210 (radiation of energy from the energy radiation unit 210, movement of the treatment portion 200 in the lumen 113 of the shaft 110, and the like) may be performed by, for example, the medical device such as a treatment robot that substitutes the operation by the operator. In this case, in the treatment, the operator or the like may control the treatment robot in a medical site such as an operating room, or may control the treatment robot in a remote place.

A combined system of the medical device 10 and the controller 300 illustrated in FIG. 1 can be provided as a medical system for performing denervation.

<Treatment Method>

Next, an example of the treatment method using the medical device 10 will be described. Hereinafter, an example will be described in which the medical device 10 is used for a procedure of enhancing the peristaltic movement of the gastrointestinal tract by applying energy to the surrounding nerve Na running around the blood vessel V (superior mesenteric artery Va) and impairing the surrounding nerve Na.

Note that, a treatment procedure described in the present specification is merely an example, and as some procedures, procedures that are not specifically described, medical instruments other than the medical device 10 used for a procedure, and the like, those known in the medical field can be appropriately adopted.

Briefly, as illustrated in FIG. 4, the treatment method according to the embodiment includes a step (S11) of delivering the guide portion 100 and the treatment portion 200 into the blood vessel V, a step (S12) of bringing the first portion 115a and the second portion 115b of the shaft 110 into contact with the inner wall Vai of the blood vessel V, a step (S13) of moving the treatment portion 200 along the lumen 113 of the shaft 110, and a step (S14) of radiating energy from the energy radiation unit 210 disposed in the lumen 113 of the shaft 110.

As illustrated in FIG. 6, the operator delivers the shaft 110 into which the treatment portion 200 is inserted to the blood vessel V. The operator can deliver the shaft 110 to the blood vessel V by using the guide wire W (see FIG. 3).

The operator brings the first portion 115a and the second portion 115b, which are formed at the distal portion of the shaft 110, into contact with the inner wall Vai of the blood vessel V. The operator can hold the shaft 110 with respect to the blood vessel V by bringing the first portion 115a and the second portion 115b into contact with the inner wall Vai of the blood vessel V. In addition, as illustrated in FIGS. 8 and 9, the operator can bring the energy radiation unit 210 close to the inner wall Vai of the blood vessel V by disposing the energy radiation unit 210 in the spiral portion 115 including the first portion 115a and the second portion 115b.

In a state where the first portion 115a and the second portion 115b are brought into contact with the inner wall Vai of the blood vessel V, the operator causes the energy radiation unit 210 disposed in the lumen 113 of the shaft 110 to radiate energy. The operator can locally apply energy to a predetermined treatment target site S.

By appropriately moving the treatment portion 200 along the spiral portion 115 in one procedure, the operator can also apply energy to different sites in the extending direction of the blood vessel V and different sites in the circumferential direction of the blood vessel V.

The operator can set a range (denervation range) in which energy is applied around the origin of the superior mesenteric artery Va to, for example, 50% or less (range of 180° or less in the circumferential direction of the blood vessel V on the transverse cross section) in an outer circumferential direction of the superior mesenteric artery Va. When the denervation range is 50% or more in the outer circumferential direction of the superior mesenteric artery Va, the enhancement of the peristaltic movement after the denervation may be excessively promoted. Therefore, it is preferable to perform denervation within the range described above.

As described above, in the medical device 10 and the treatment method according to the embodiment, by bringing the first portion 115a and the second portion 115b, which are formed in the shaft 110 of the guide portion 100, into contact with the inner wall Vai of the blood vessel V, the shaft 110 can be held with respect to the blood vessel V. In a state where the shaft 110 is held with respect to the blood vessel V, the operator can locally radiate energy to the treatment target site S by moving the treatment portion 200 along the lumen 113 of the shaft 110 and disposing the energy radiation unit 210 of the treatment portion 200 at the position close to the inner wall Vai of the blood vessel V. Therefore, it is possible to perform denervation more reliably while suppressing the energy radiated from the energy radiation unit 210 to a low level.

Next, a modification example of the above-described embodiment will be described. In the description of the modification example, a member, a treatment procedure, and the like already described are appropriately omitted. In addition, contents that are not particularly described in the modification example can be the same as those in the above-described embodiment.

Modification Example 1

Figure 10:
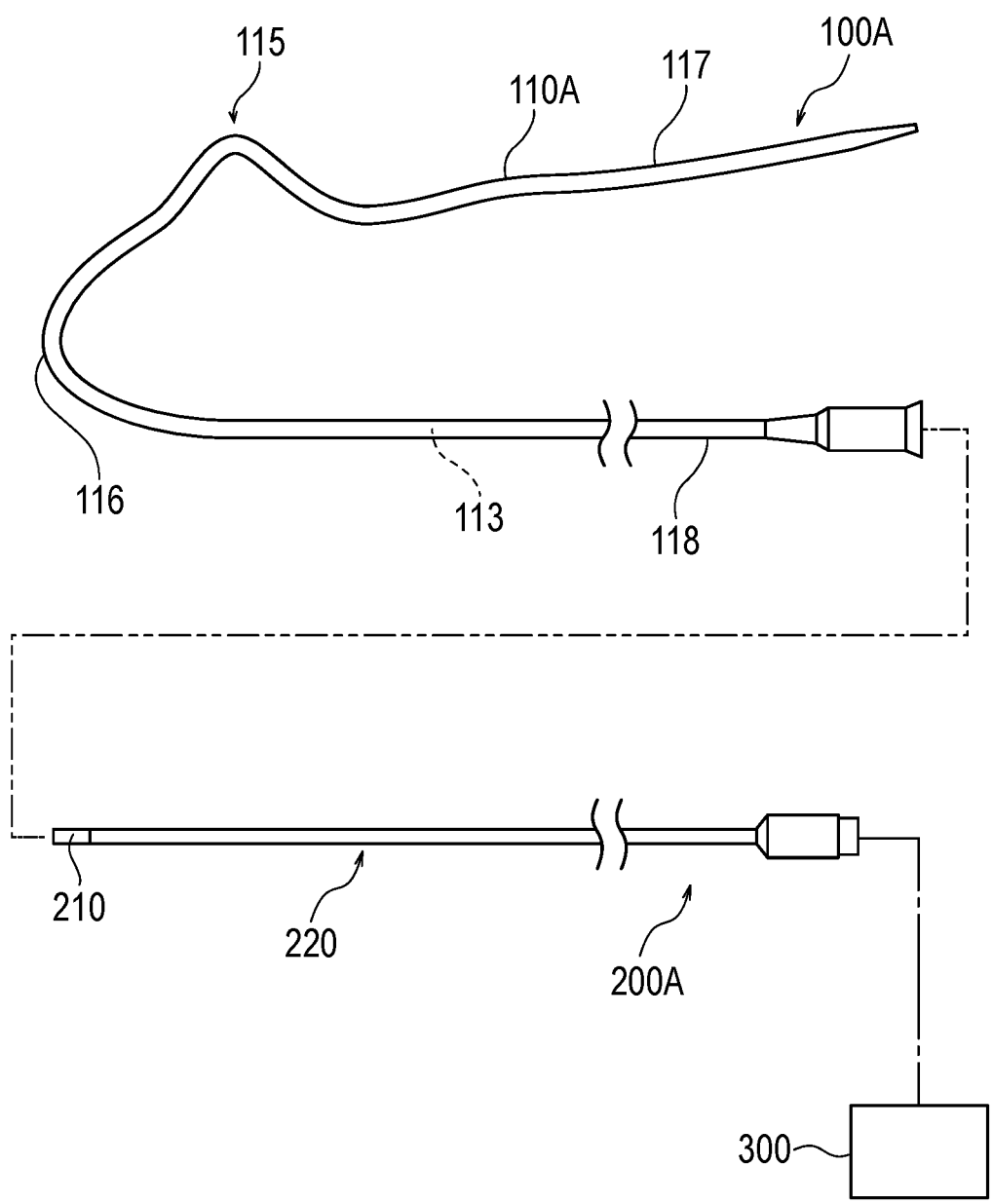
FIG. 10 is a view schematically illustrating an overall configuration of a medical device according to Modification example 1.

FIG. 10 illustrates a medical device 10A according to Modification example 1.

As illustrated in FIG. 10, in the medical device 10A, a guide portion 100A and a treatment portion 200A are configured as separate catheter devices.

When performing a treatment using the medical device 10A, the operator inserts the energy radiation unit 210 and the main body portion 220 of the treatment portion 200A into the lumen 113 of a shaft 110A. Similarly to the procedure described in the above-described embodiment, in a state where the first portion 115a of the shaft 110A and the second portion 115b of the shaft 110A are brought into contact with the inner wall Vai of the blood vessel V, the operator causes the energy radiation unit 210 disposed in the lumen 113 of the shaft 110A to radiate energy, thereby locally applying the energy to the treatment target site S.

Note that, each of the guide portion 100A and the treatment portion 200A described in the modification example can be configured independently as a medical instrument used for a procedure of radiating energy from the inside of the blood vessel V and denervating the surrounding nerve Na existing outside the blood vessel V. That is, the guide portion 100A can be configured as a guide device, and the treatment portion 200A can be configured as a treatment device.

Modification Example 2

Figure 11:
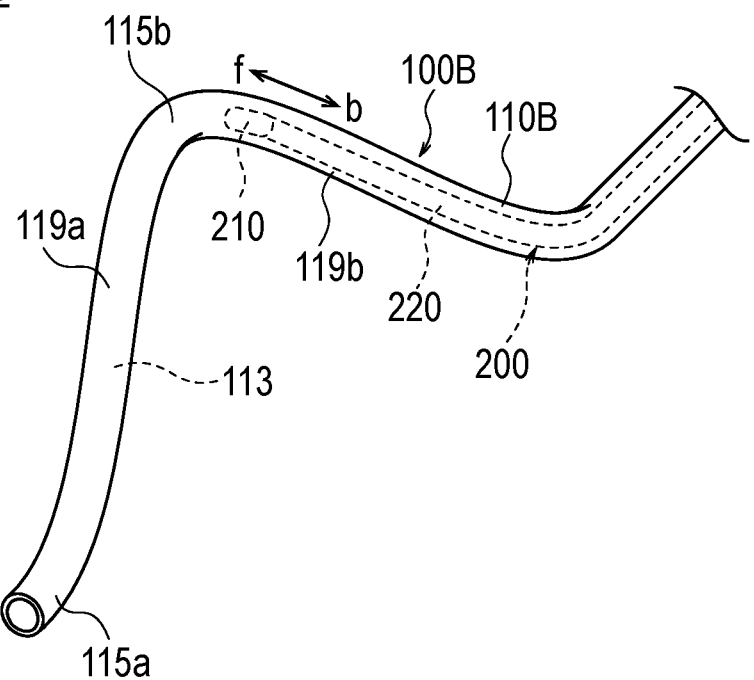
FIG. 11 is an enlarged perspective view illustrating a distal portion of a shaft of a medical device according to a modification example 2.
Figure 12:
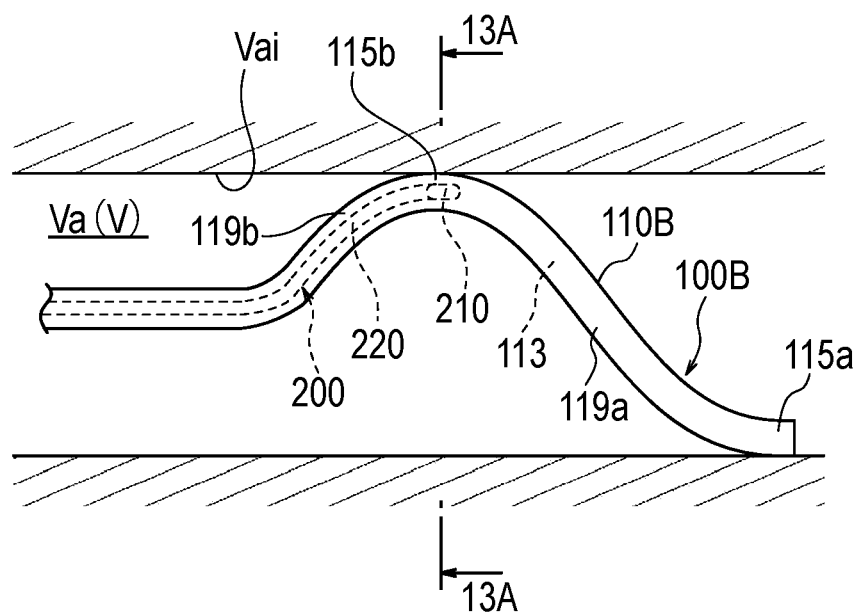
FIG. 12 is a cross-sectional view of a blood vessel schematically illustrating a usage example of a medical device according to Modification example 2.
Figure 13:
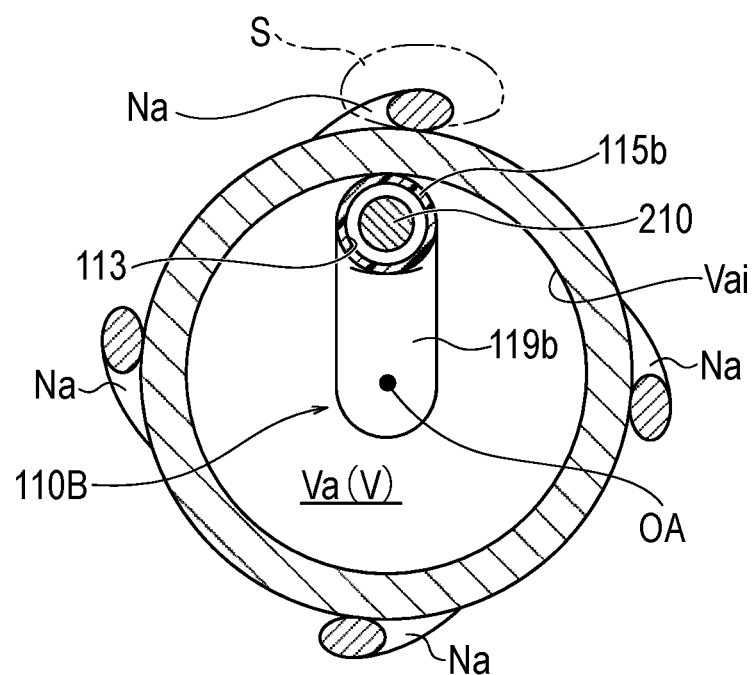
FIG. 13 is a cross-sectional view (transverse cross-sectional view) of a blood vessel taken along an arrow 13A-13A illustrated in FIG. 12.

FIG. 11 illustrates a medical device 10B according to Modification example 2. FIGS. 12 and 13 schematically illustrate an example of a treatment method using the medical device 10B according to Modification example 2. Note that, FIG. 13 is a transverse cross-sectional view of the blood vessel V taken along an arrow 13A-13A illustrated in FIG. 12.

In the medical device 10 according to the above-described embodiment, the spiral portion 115 is formed at the distal portion of the shaft 110 of the guide portion 100 (see FIG. 2). On the other hand, the spiral portion 115 is not formed in a shaft 110B included in a guide portion 100B of the medical device 10B according to Modification example 2.

As illustrated in FIG. 11, a distal portion of the shaft 110B according to Modification example 2 has a shape curved in a direction intersecting with an axial direction of the shaft 110B.

As illustrated in FIG. 12, the distal end of the shaft 110B forms a first portion 115a that can come into contact with the inner wall Vai of the blood vessel V.

A top of the curved portion disposed on the proximal side of the shaft 110B with respect to the first portion 115a forms a second portion 115b that can come into contact with the inner wall Vai of the blood vessel V.

In the treatment using the medical device 10B according to Modification example 2, as illustrated in FIG. 12, the operator can dispose the first portion 115a and the second portion 115b so as to be brought into point contact with the inner wall Vai of the blood vessel V.

The first portion 115a and the second portion 115b come into contact with the inner wall Vai of the blood vessel V at different positions in the extending direction of the blood vessel V.

As illustrated in FIGS. 12 and 13, an angle of 180° is formed along the circumferential direction of the blood vessel V between the first portion 115a and the second portion 115b. Therefore, the first portion 115a and the second portion 115b can be disposed at positions facing each other with a center OA interposed therebetween on the transverse cross section of the blood vessel V.

The angle between the first portion 115a and the second portion 115b is not particularly limited as long as the first portion 115a and the second portion 115b can be disposed at different positions on the transverse cross section of the blood vessel V. That is, the angle between the first portion 115a and the second portion 115b may be an angle other than 180°.

As illustrated in FIGS. 11 and 12, the operator can dispose a portion 119a formed between the first portion 115a and the second portion 115b in the shaft 110B and a portion 119b formed on the proximal side with respect to the second portion 115b in the shaft 110B so as not to come into contact with the inner wall Vai of the blood vessel V.

The operator can bring the energy radiation unit 210 close to the inner wall Vai of the blood vessel V by disposing the energy radiation unit 210 in the first portion 115a brought into contact with the inner wall Vai of the blood vessel V. The operator can locally apply energy to the treatment target site S by causing the energy to be radiated from the energy radiation unit 210 brought close to the inner wall Vai of the blood vessel V.

In addition, the operator can bring the energy radiation unit 210 close to the inner wall Vai of the blood vessel V by disposing the energy radiation unit 210 in the second portion 115b brought into contact with the inner wall Vai of the blood vessel V.

As illustrated in FIGS. 12 and 13, the second portion 115b is disposed at a position different from that of the first portion 115a in the extending direction of the blood vessel V and the circumferential direction of the blood vessel V. Therefore, by causing energy to be radiated from the energy radiation unit 210 disposed in the second portion 115b, the operator can apply the energy to a site different from the site in which the first portion 115a is disposed in the extending direction of the blood vessel V and the circumferential direction of the blood vessel V. By causing energy to be radiated from the energy radiation unit 210 disposed in the second portion 115b, the operator can locally apply the energy to the treatment target site S similarly to the case of causing the energy to be radiated from the energy radiation unit 210 disposed in the first portion 115a.

The medical device 10B according to Modification example 2 is configured such that the first portion 115a and the second portion 115b, which are formed in the shaft 110B of the guide portion 100B, come into point contact with the inner wall Vai of the blood vessel V. Therefore, when the first portion 115a and the second portion 115b are brought into contact with the inner wall Vai of the blood vessel V, a load applied to the blood vessel V can be reduced.

A curvature of the portions forming the first portion 115a and the second portion 115b in the shaft 110B, an axial distance between the first portion 115a and the second portion 115b, and the like are not particularly limited, and can be arbitrarily changed.

Modification Example 3

Figure 14:
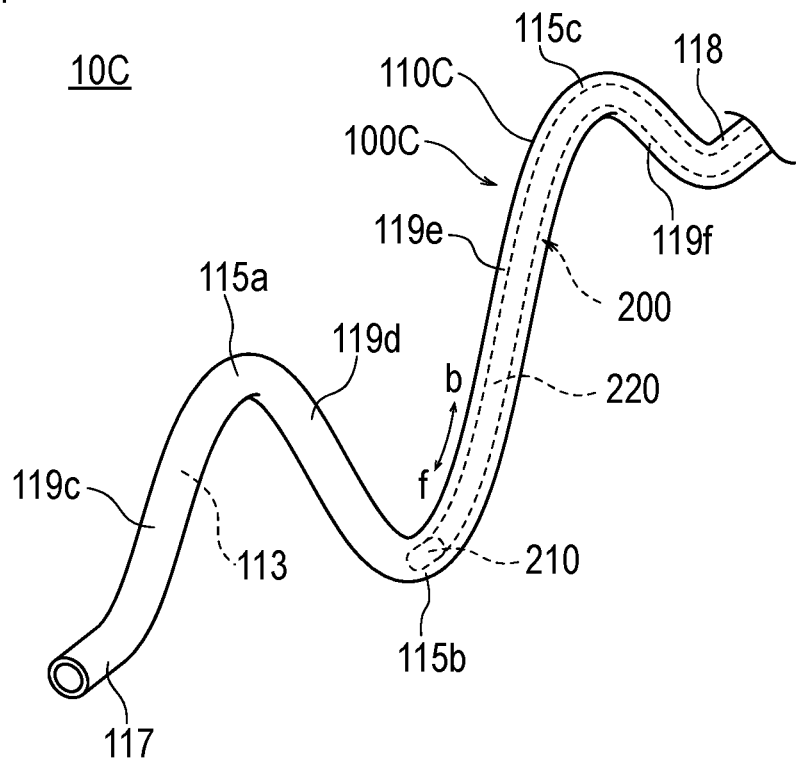
FIG. 14 is an enlarged perspective view illustrating a distal portion of a medical device according to Modification example 3.
Figure 15:
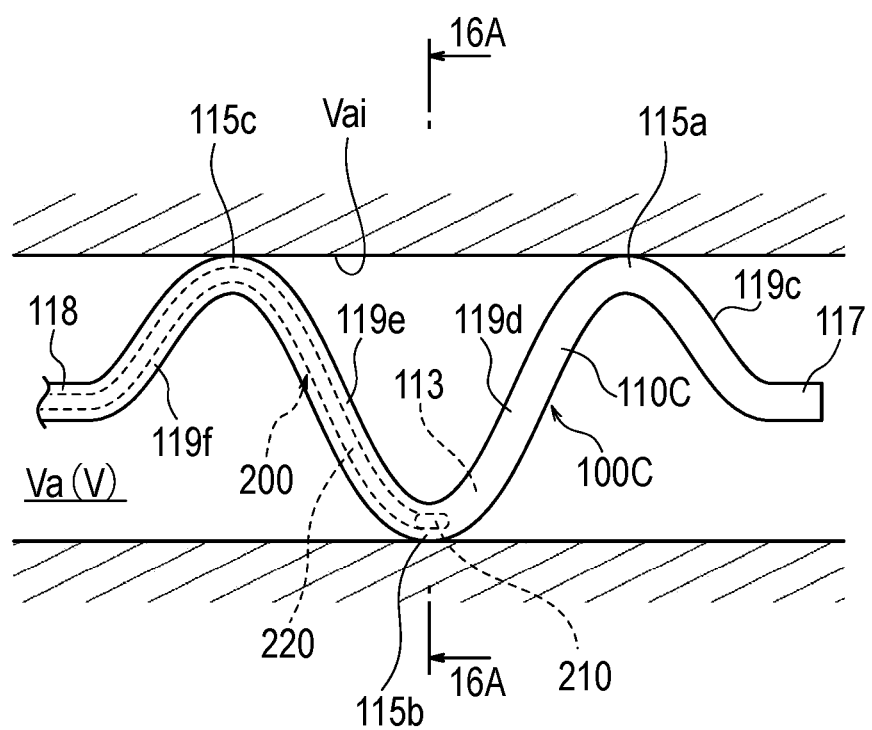
FIG. 15 is a cross-sectional view of a blood vessel schematically illustrating a usage example of a medical device according to Modification example 3.
Figure 16:
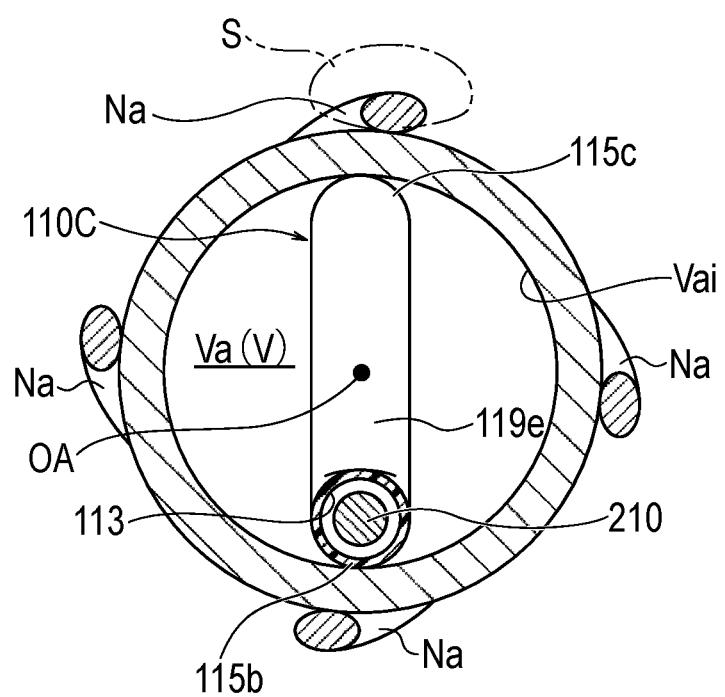
FIG. 16 is a cross-sectional view (transverse cross-sectional view) of a blood vessel taken along an arrow 16A-16A illustrated in FIG. 15.

FIG. 14 illustrates a medical device 10C according to Modification example 3. FIGS. 15 and 16 schematically illustrate an example of a treatment method using the medical device 10C according to Modification example 3. Note that, FIG. 16 is a transverse cross-sectional view of the blood vessel V taken along an arrow 16A-16A illustrated in FIG. 15.

The medical device 10C according to Modification example 3 is configured such that the first portion 115a and the second portion 115b come into point contact with the inner wall Vai of the blood vessel V, similarly to the medical device 10B according to Modification example 2. Furthermore, the medical device 10C includes a third portion 115c formed on the proximal side of a shaft 110C with respect to the second portion 115b.

In the shaft 110C, portions forming the first portion 115a, the second portion 115b, and the third portion 115c are curved in the axial direction of the shaft 110C. Therefore, the shaft 110C has a zigzag shape bent a plurality of times in the axial direction of the shaft 110C.

As illustrated in FIGS. 15 and 16, the operator can bring each of the first portion 115a, the second portion 115b, and the third portion 115c into contact with the inner wall Vai of the blood vessel V. The operator can bring the energy radiation unit 210 close to the inner wall Vai of the blood vessel V by disposing the energy radiation unit 210 in the first portion 115a, the second portion 115b, and the third portion 115c.

The operator can dispose a portion 119c formed between the first portion 115a and the distal side portion 117, a portion 119d formed between the first portion 115a and the second portion 115b, a portion 119e formed between the second portion 115b and the third portion 115c, and a portion 119f formed between the third portion 115c and the proximal side portion 118 so as not to come into contact with the inner wall Vai of the blood vessel V.

The medical device 10C according to Modification example 3 is configured such that the first portion 115a, the second portion 115b, and the third portion 115c, which are formed in the shaft 110C of the guide portion 100C, come into point contact with the inner wall Vai of the blood vessel V. Therefore, when the first portion 115a, the second portion 115b, and the third portion 115c are brought into contact with the inner wall Vai of the blood vessel V, a load applied to the blood vessel V can be reduced.

A curvature of the portions forming the first portion 115a, the second portion 115b, and the third portion 115c in the shaft 110C, a distance between the portions 115a, 115b, and 115c in an axial direction, the number of curved portions forming the zigzag shape, and the like are not particularly limited, and can be arbitrarily changed.

Modification Example 4

Figure 17:
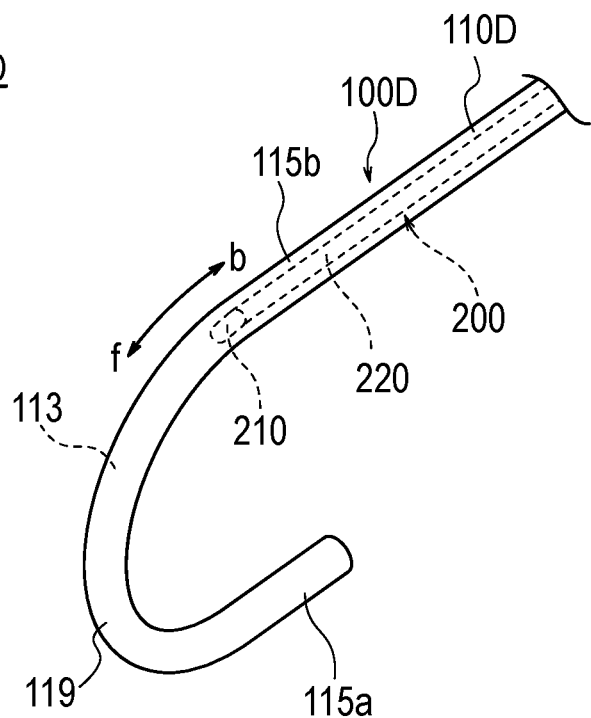
FIG. 17 is an enlarged perspective view illustrating a distal portion of a medical device according to Modification example 4.
Figure 18:
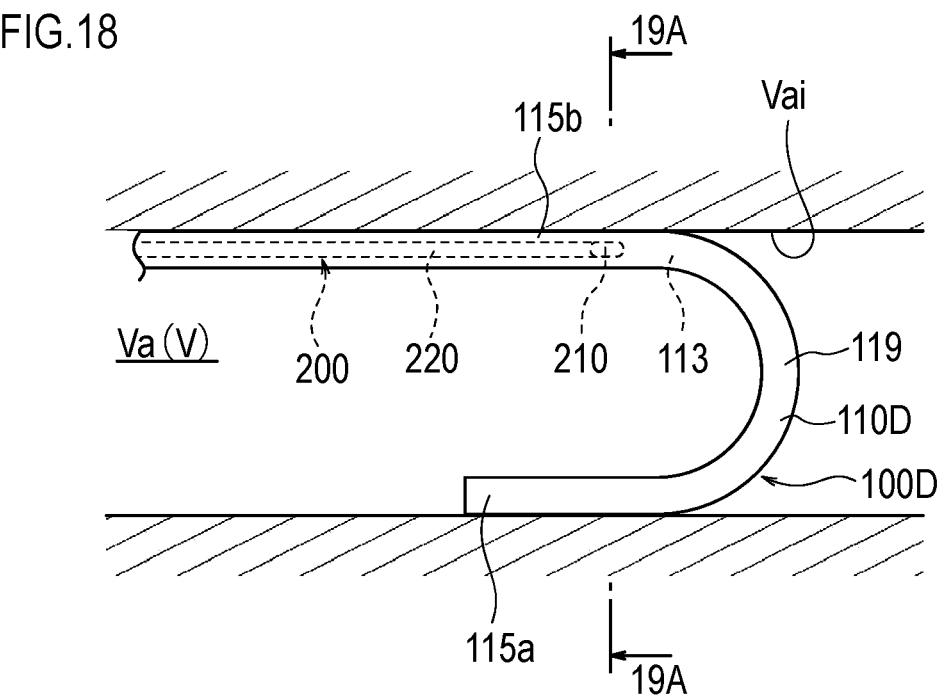
FIG. 18 is a cross-sectional view of a blood vessel schematically illustrating a usage example of a medical device according to Modification example 4.
Figure 19:
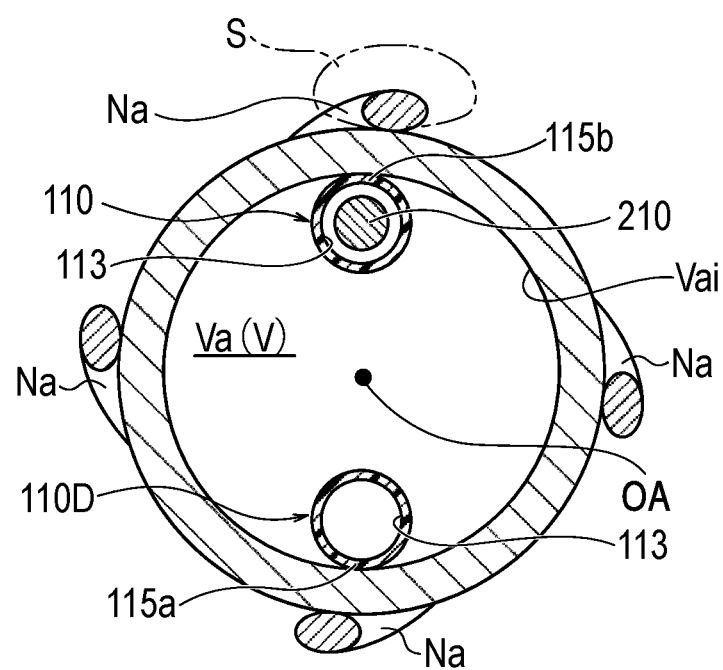
FIG. 19 is a cross-sectional view (transverse cross-sectional view) of a blood vessel taken along an arrow 19A-19A illustrated in FIG. 18.

FIG. 17 illustrates a medical device 10D according to Modification example 4. FIGS. 18 and 19 schematically illustrate an example of a treatment method using the medical device 10D according to Modification example 4. Note that, FIG. 19 is a transverse cross-sectional view of the blood vessel V taken along an arrow 19A-19A illustrated in FIG. 18.

A shaft 110D included in a guide portion 100D of the medical device 10D according to Modification example includes a middle portion 119 disposed between the first portion 115a and the second portion 115b.

The middle portion 119 is curved from a distal side of the shaft 110D toward a proximal side of the shaft 110D.

A portion forming the first portion 115a in the shaft 110D and a peripheral portion thereof extend substantially linearly. A portion forming the second portion 115b in the shaft 110D and a peripheral portion thereof extend substantially linearly.

As illustrated in FIGS. 18 and 19, the operator can bring the first portion 115a, and the second portion 115b into contact with the inner wall Vai of the blood vessel V. The operator can bring the energy radiation unit 210 close to the inner wall Vai of the blood vessel V by disposing the energy radiation unit 210 in the first portion 115a, and the second portion 115b.

The operator can dispose the shaft 110D such that the middle portion 119 does not come into contact with the inner wall Vai of the blood vessel V.

In the medical device 10D according to Modification example 4, the first portion 115a and the second portion 115b, which are formed in the shaft 110D, extend substantially linearly. Therefore, when the shaft 110D is disposed in the blood vessel V, the operator can bring the first portion 115a and the second portion 115b into contact with the inner wall Vai of the blood vessel V along the extending direction of the blood vessel V in a relatively long range. As a result, the operator can increase a holding force of the shaft 110D with respect to the inner wall Vai of the blood vessel V. In addition, the operator can locally apply energy to the treatment target site S by causing the energy to be radiated from the energy radiation unit 210 disposed in the first portion 115a and the second portion 115b.

Note that, an axial length of the portions forming the first portion 115a and the second portion 115b in the shaft 110D, a curvature of the middle portion 119, and the like are not particularly limited, and can be arbitrarily changed. In addition, the first portion 115a and the second portion 115b may not extend linearly. For example, the first portion 115a and the second portion 115b may not be disposed at positions facing each other.

Modification Example 5

Figure 20:
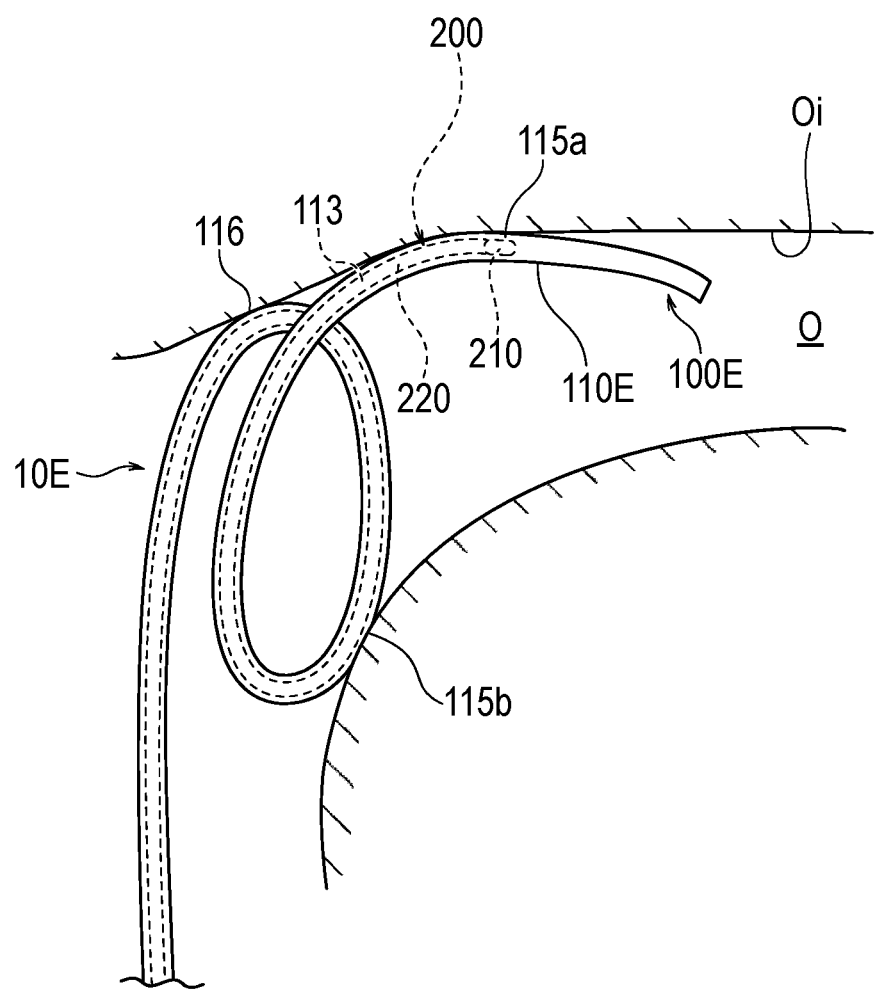
FIG. 20 is a cross-sectional view of a living organ schematically illustrating a usage example of a medical device according to Modification example 5.

FIG. 20 illustrates an example of a treatment method using a medical device 10E according to Modification example 5.

In the above-described embodiment, the blood vessel V (superior mesenteric artery Va) has been exemplified as the living organ to be treated by the medical device 10. However, the living organ to be treated by the medical device is not limited to only the blood vessel, and may be a bile duct, a trachea, an esophagus, a urethra, an ear and nose lumen, or the like. As an example, the medical device can be configured as a device for applying energy to a sympathetic nerve existing outside of renal arteries of a patient by causing the energy to be radiated from the energy radiation unit disposed in a renal artery and lowering a blood pressure of the patient. In addition, as another example, the medical device can be configured as a device for expanding bronchial tubes of the patient by causing the energy to be radiated from the energy radiation unit disposed in the bronchial tubes.

FIG. 20 illustrates an example in which the medical device 10E is used for the treatment of a pulmonary vein O. The first portion 115a and the second portion 115b of a shaft 110E included in a guide portion 100E of the medical device 10E can be brought into contact with an inner wall Oi of the pulmonary vein O. The operator can locally apply energy by causing the energy to be radiated from the energy radiation unit 210 disposed in the first portion 115a and the second portion 115b of the shaft 110E. Therefore, treatment and recovery from a disease such as an atrial fibrillation can be achieved.

As described above, the medical device and the treatment method according to the present invention have been described in the embodiment, but the present invention is not limited only to the contents described in the specification, and can be appropriately changed based on the description of the scope of the claims.

As long as the medical device includes a guide portion including a shaft in which a first portion and a second portion are formed, and a treatment portion configured to be insertable into a lumen of the guide portion, a specific configuration of the medical device is not limited. For example, as long as the effect of the present invention are exerted, a material, a shape, a size, an arrangement of each member included in the guide portion and the treatment portion, a connection structure between the members, and the like are not particularly limited, and can be arbitrarily changed and replaced.

In addition, in the medical device, any component member or the like not specifically described in the specification can be appropriately added, and the additional member described in the specification can be appropriately omitted. In addition, in the treatment method, any procedure not specifically described in the specification can be appropriately added, and the additional procedure described in the specification can be appropriately omitted. In addition, in the treatment method, the order of procedures can be appropriately replaced as long as the effect of the invention can be exhibited.

REFERENCE SIGNS LIST 10, 10A, 10B, 10C, 10D, 10E Medical device
100, 100A, 100B, 100C, 100D, 100E Guide portion
110, 110A, 110B, 110C, 110D, 110E Shaft
110a Distal end opening portion of shaft
113 Lumen of shaft
113a Space portion
114 Filling member
114a Guide wire lumen
115 Spiral portion
115a First portion
115b Second portion
115c Third portion
116 Curved portion
117 Distal side portion
118 Proximal side portion
119 Middle portion
120 Hub
121 Operation unit
200, 200A Treatment portion
210 Energy radiation unit
220 Main body portion
230 Auxiliary member
300 Controller
A Reference axis
W Guide wire
Na Surrounding nerve (extravascular nerve)
S Treatment target site
V Blood vessel (biological lumen)
Va Superior mesenteric artery
Vai Inner wall
Vb celiac artery
Vc Inferior mesenteric artery
Vd Aorta
O Pulmonary vein
Oi Inner wall of pulmonary vein

The invention claimed is:

1. A medical device comprising:
a guide portion that includes a tube-shaped body shaft in which a lumen is formed and is insertable into a living organ; and
a treatment portion that includes an energy radiation unit capable of radiating energy capable of reaching a surrounding nerve existing outside the living organ, the treatment portion being disposed in the lumen of the tube-shaped body shaft,
wherein the tube-shaped body shaft has a spiral portion including a first portion and a second portion at a distal portion of the tube-shaped body shaft, the first portion is configured to be capable of coming into contact with an inner wall of the living organ, and the second portion is disposed on a proximal side of the tube-shaped body shaft with respect to the first portion and configured to be capable of coming into contact with the inner wall of the living organ at a position different from that of the first portion on a transverse cross section of the inner wall of the living organ, and each of the first portion and the second portion consists of a cylindrical tube as at least a part of the tube-shaped body shaft, and the each of the first portion and the second portion has at least a part of the lumen, the treatment portion is movable in the lumen of the tube-shaped body shaft in a state where at least a part of the first portion and at least a part of the second portion come into contact with the inner wall of the living organ, and the tube-shaped body shaft includes a curved portion in a natural state where an external force is not applied, and the curved portion is positioned apart from the spiral portion and is positioned on the proximal side with respect to the second portion, the tube-shaped body shaft shows a flexibility in response to the external force, when the external force is removed from the tube-shaped body shaft, the curved portion assumes a curved shape, and the curved shape is formed such that a distal end of the tube-shaped body shaft points back to a proximal portion of the tube-shaped body shaft.

2. The medical device according to claim 1, wherein the tube-shaped body shaft is configured to continuously bring a portion from the first portion to the second portion into contact with the inner wall of the living organ.

3. The medical device according to claim 2, wherein at the distal portion of the tube-shaped body shaft, the spiral portion extending spirally is formed in the portion from the first portion to the second portion.

4. The medical device according to claim 1, wherein the tube-shaped body shaft is configured to bring the each of the first portion and the second portion into point contact with the inner wall of the living organ.

5. The medical device according to claim 4, wherein at the distal portion of the tube-shaped body shaft, a zigzag shape is formed by the first portion and the second portion.

6. The medical device according to claim 1, further comprising a middle portion that is disposed between the first portion and the second portion, wherein the middle portion is curved from the distal portion of the tube-shaped body shaft toward the proximal side of the tube-shaped body shaft.

7. The medical device according to claim 1, wherein the curved portion is configured by deflecting a portion positioned on the distal portion of the tube-shaped body shaft with respect to the curved portion to a portion positioned on the proximal side of the tube-shaped body shaft with respect to the curved portion.

8. The medical device according to claim 1, wherein the guide portion includes the tube-shaped body shaft and a hub disposed at the proximal portion of the tube-shaped body shaft, the treatment portion includes the energy radiation unit and a main body portion in which the energy radiation unit is disposed at a distal portion and which is inserted into the lumen of the tube-shaped body shaft, and the guide portion and the treatment portion constitute a catheter device in a state where the guide portion and the treatment portion are integrally assembled.

9. The medical device according to claim 1, wherein the living organ is at least one blood vessel selected from the group consisting of a superior mesenteric artery, a celiac artery, and an inferior mesenteric artery, and a peristaltic movement of a gastrointestinal tract is enhanced by applying the energy radiated from the energy radiation unit disposed in the lumen of the tube-shaped body shaft disposed in the blood vessel to the surrounding nerve innervating the gastrointestinal tract to completely or partially block an autonomic neural transmission.

10. The medical device according to claim 1, wherein the energy radiation unit is configured to be capable of radiating a microwave or an ultrasonic wave.

11. The medical device according to claim 1, wherein the tube-shaped body shaft has a substantially linear portion positioned between the distal end of the tube-shaped body shaft and the spiral portion.

12. A treatment method comprising:

inserting a guide portion into a living organ, the guide portion including a tube-shaped body shaft in which a lumen is formed, and the tube-shaped body shaft having a spiral portion including a first portion and a second portion;

bringing the first portion formed at a distal portion of the tube-shaped body shaft into contact with an inner wall of the living organ and bringing the second portion formed on a proximal side of the tube-shaped body shaft with respect to the first portion into contact with a position different from that of the first portion on a transverse cross section of the inner wall of the living organ, wherein each of the first portion and the second portion consists of a cylindrical tube as at least a part of the tube-shaped body shaft, the each of the first portion and the second portion has at least a part of the lumen, the tube-shaped body shaft includes a curved portion in a natural state where an external force is not applied, the curved portion is positioned apart from the spiral portion and is positioned on the proximal side with respect to the second portion, the tube-shaped body shaft shows a flexibility in response to the external force, when the external force is removed from the tube-shaped body shaft, the curved portion assumes a curved shape, and the curved shape is formed such that a distal end of the tube-shaped body shaft points back to a proximal side portion of the tube-shaped body shaft;

moving a treatment portion including an energy radiation unit by a predetermined distance along the lumen of the tube-shaped body shaft in a state where the first portion and the second portion are brought into contact with the inner wall of the living organ; and applying energy to a surrounding nerve existing outside the living organ by causing the energy to be radiated from the energy radiation unit in a state where the energy radiation unit is disposed in the lumen of the tube-shaped body shaft.

13. The treatment method according to claim 12, wherein the treatment portion is moved by a predetermined distance along the lumen of the tube-shaped body shaft in a state where a portion from the first portion to the second portion is disposed so as to be continuously brought into contact with the inner wall of the living organ.

14. The treatment method according to claim 12, wherein the treatment portion is moved by a predetermined distance along the lumen of the tube-shaped body shaft in a state where the each of the first portion and the second portion is brought into point contact with the inner wall of the living organ.

15. The treatment method according to claim 12, wherein the tube-shaped body shaft includes a middle portion disposed between the first portion and the second portion and curved from the distal portion of the tube-shaped body shaft toward the proximal side of the tube-shaped body shaft.

16. The treatment method according to claim 12, wherein the treatment portion is moved along at least a part of the first portion and at least a part of the second portion, which are brought into contact with the inner wall of the living organ, in a state where a part of the tube-shaped body shaft positioned on the distal portion with respect to the curved portion is deflected to a portion positioned on a proximal side with respect to the curved portion.

17. The treatment method according to claim 12, wherein the living organ is at least one blood vessel selected from the group consisting of a superior mesenteric artery, a celiac artery, and an inferior mesenteric artery,
- the energy radiation unit is disposed in the lumen of the tube-shaped body shaft disposed in the blood vessel, and
- a peristaltic movement of a gastrointestinal tract is enhanced by applying the energy radiated from the energy radiation unit to the surrounding nerve innervating the gastrointestinal tract to completely or partially block an autonomic neural transmission.

18. The treatment method according to claim 12, wherein a microwave or an ultrasonic wave is radiated as the energy from the energy radiation unit.

* * * * *